(12) United States Patent
Bruneau

(10) Patent No.: US 8,501,760 B2
(45) Date of Patent: *Aug. 6, 2013

(54) PHARMACEUTICAL COMPOSITIONS COMPRISING NILOTINIB OR ITS SALT

(71) Applicant: Novartis AG, Basel (CH)

(72) Inventor: Nathalie Bruneau, Cran-Gevrier (FR)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/624,354

(22) Filed: Sep. 21, 2012

(65) Prior Publication Data

US 2013/0023549 A1 Jan. 24, 2013

Related U.S. Application Data

(62) Division of application No. 12/442,544, filed as application No. PCT/EP2007/060165 on Sep. 25, 2007, now Pat. No. 8,293,756.

(30) Foreign Application Priority Data

Sep. 27, 2006 (EP) .................................. 06121371

(51) Int. Cl.
*A61K 31/506* (2006.01)

(52) U.S. Cl.
USPC ........... 514/275; 514/256; 514/247; 514/183; 544/331; 544/330; 544/322; 544/242; 544/224

(58) Field of Classification Search
None
See application file for complete search history.

(56) References Cited

U.S. PATENT DOCUMENTS

| 4,072,535 | A | 2/1978 | Short et al. |
| 6,346,537 | B1 | 2/2002 | Hata et al. |
| 8,163,904 | B2 * | 4/2012 | Manley et al. ............. 544/331 |
| 8,293,756 | B2 * | 10/2012 | Bruneau ..................... 514/275 |
| 8,343,984 | B2 * | 1/2013 | Manley et al. .............. 514/269 |
| 2004/0229821 | A1 | 11/2004 | Kim et al. |
| 2005/0031693 | A1 | 2/2005 | Babcock et al. |
| 2006/0006258 | A1 | 1/2006 | Remon et al. |
| 2006/0013871 | A1 | 1/2006 | Berger et al. |
| 2006/0159762 | A1 | 7/2006 | Stanic Ljubin et al. |
| 2006/0257482 | A1 | 11/2006 | Kumar et al. |
| 2008/0200487 | A1 | 8/2008 | Manley et al. |
| 2008/0269269 | A1 | 10/2008 | Manley et al. |
| 2010/0038816 | A1 | 2/2010 | Ghogh et al. |

FOREIGN PATENT DOCUMENTS

| WO | WO 2004/005281 | 1/2004 |
| WO | 2005/039586 A1 | 5/2005 |
| WO | WO 2006/079539 | 8/2006 |
| WO | WO 2006/089781 | 8/2006 |
| WO | WO 2007/015870 | 2/2007 |
| WO | WO 2007/015871 | 2/2007 |

OTHER PUBLICATIONS

"Clinical pharmacokinetics (PK) of AMN107, a novel inhibitor of Bcr-Abl, in healthy subjects and patients with imatinib resistant or intolerant chronic myelogenous leukemia (CML) or relapsed/refractory Ph+ acute lymphocytic leukemia (Ph+ALL)" by Tanaka et al., J. Clin. Oncol. 24, Abstract No. 3095 (Jun. 2006).*

"Scientific Discussion," EMEA, 2007 retrieved from http://www.ema.europa.eu/docs/en_GB/document.library/EPAr—ScientificDiscussion/human/00079B/WC500634398.pdf M. Matsumoto et al. (ED.), Manual of Pharmaceutics, Pharmaceutical Sciences, Chapter 6.1.3, Granules, p. 83-85 and Chapter 7-2-3, Granulation, p. 112-113, Nanzando, Co., Ltd., 1989.

* cited by examiner

*Primary Examiner* — Brandon Fetterolf
*Assistant Examiner* — Theodore R West
(74) *Attorney, Agent, or Firm* — Stephen Johnson

(57) ABSTRACT

A pharmaceutical composition, especially capsules, comprising granules containing nilotinib or a salt thereof with at least one pharmaceutically acceptable excipient. The granules may be produced by a wet granulation process.

6 Claims, No Drawings

PHARMACEUTICAL COMPOSITIONS COMPRISING NILOTINIB OR ITS SALT

FIELD OF THE INVENTION

The present invention relates to a pharmaceutical composition comprising a therapeutic compound of formula I (see below), for example nilotinib. Such a pharmaceutical composition may be prepared by a wet granulation process for preparing granules that are subsequently filled into a capsule.

BACKGROUND OF THE INVENTION

Nilotinib is 4-Methyl-3-[[4-(3-pyridinyl)-2-pyrimidinyl]amino]-N-[5-(4-methyl-1H-imidazol-1-yl)-3-(trifluoromethyl)phenyl]benzamide. A particularly useful salt of nilotinib is nilotinib hydrochloride monohydrate. These therapeutic compounds have utility as inhibitors of the protein tyrosine kinase (TK) activity of Bcr-Abl. Examples of conditions that may be treated by such therapeutic compounds include, but are not limited to, chronic myeloid leukemia and gastrointestinal stromal tumors.

There is a need to formulate nilotinib and the other therapeutic compounds hereinafter disclosed into pharmaceutical compositions, especially solid oral dosage forms, such that the therapeutic benefits of the compounds may be delivered to a patient in need thereof. Posing a challenge resolving this need is the physiochemical properties of such therapeutic compounds. Nilotinib and its salts are poorly water soluble compounds and are difficult to formulate and deliver (i.e., made bioavailable when ingested orally). An object of the present invention is to provide an exemplary solution by making a pharmaceutical composition in the form of a solid oral dosage form that may be ingested by a patient.

SUMMARY OF THE INVENTION

The present invention provides for a novel pharmaceutical composition that comprises a therapeutic compound of formula I, for example, nilotinib or a salt thereof. The pharmaceutical compositions are in the form of solid oral dosage forms, especially capsules. The capsules are filled with granules of the therapeutic compound blended with an external phase comprising at least one pharmaceutically acceptable excipient. A particularly useful process for making the granules is a wet granulation process. The therapeutic compound and any pharmaceutically acceptable excipients, for example a surfactant, are wet massed with purified water (or organic solvents) and subsequently dried to form granules. An example of a particularly useful surfactant, is a poloxamer such as poloxamer 188. It has been found that the use of a surfactant allows for a decrease in concentration of other excipients (such as lubricants).

In another exemplary embodiment of the present invention, the wet granulation process to prepare granules includes the following steps: a) forming a powder blend of the therapeutic compound (e.g., nilotinib or a salt thereof) and at least one pharmaceutically acceptable excipient; b) adding a granulation liquid to the powder blend under agitation to form a wet mass; c) granulating the wet mass to form moist granules and d) drying the moist granules.

DETAILED DESCRIPTION OF THE INVENTION

The present invention relates pharmaceutical compositions comprising a therapeutic compound. Such pharmaceutical compositions may be prepared by subjecting the therapeutic compound to wet granulation with a granulation liquid to form granules or a granuled mixture. The granules or granuled mixture may be subsequently encapsulated into hard gelatin capsules, compressed into tablets, or filled into sachets to form solid oral dosage forms.

As used herein, the term "therapeutic compound" refers to pyrimidylaminobenzamide compounds of formula I:

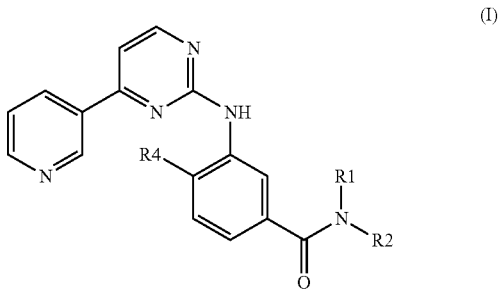

(I)

wherein $R_1$ represents hydrogen, lower alkyl, lower alkoxy-lower alkyl, acyloxy-lower alkyl, carboxy-lower alkyl, lower alkoxycarbonyl-lower alkyl, or phenyl-lower alkyl;

$R_2$ represents hydrogen, lower alkyl, optionally substituted by one or more identical or different radicals $R_3$, cycloalkyl, benzcycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted;

and $R_3$ represents hydroxy, lower alkoxy, acyloxy, carboxy, lower alkoxycarbonyl, carbamoyl, N-mono- or N,N-disubstituted carbamoyl, amino, mono- or disubstituted amino, cycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted;

or wherein $R_1$ and $R_2$ together represent alkylene with four, five or six carbon atoms optionally mono- or disubstituted by lower alkyl, cycloalkyl, heterocyclyl, phenyl, hydroxy, lower alkoxy, amino, mono- or disubstituted amino, oxo, pyridyl, pyrazinyl or pyrimidinyl; benzalkylene with four or five carbon atoms; oxaalkylene with one oxygen and three or four carbon atoms; or azaalkylene with one nitrogen and three or four carbon atoms wherein nitrogen is unsubstituted or substituted by lower alkyl, phenyl-lower alkyl, lower alkoxycarbonyl-lower alkyl, carboxy-lower alkyl, carbamoyl-lower alkyl, N-mono- or N,N-disubstituted carbamoyl-lower alkyl, cycloalkyl, lower alkoxycarbonyl, carboxy, phenyl, substituted phenyl, pyridinyl, pyrimidinyl, or pyrazinyl;

$R_4$ represents hydrogen, lower alkyl, or halogen;

and a N-oxide and to the pharmaceutically acceptable salts of such a compound. Such therapeutic compounds are suitable for the preparation of a pharmaceutical composition for the treatment of kinase dependent diseases, especially Bcr-Abl and Tie-2 kinase dependent diseases, for example, as drugs to treat one or more proliferative diseases.

Within the definition of "therapeutic compound," the prefix "lower" denotes a radical having up to and including a maximum of seven, especially up to and including a maximum of four carbon atoms, the radicals in question being either linear or branched with single or multiple branching.

As used herein, where the plural form is used for compounds, salts, and the like, this is taken to mean also a single compound, salt, or the like.

Any asymmetric carbon atoms may be present in the (R)-, (S)- or (R,S)-configuration, for example in the (R)- or (S)-configuration. The compounds may thus be present as mixtures of isomers or as pure isomers, for example as enantiomer-pure diastereomers. Also contemplated within the present invention is the use of any possible tautomers of the compounds of formula I.

Lower alkyl is for example alkyl with from and including one up to and including seven, for example from and including one to and including four, and is linear or branched; for example, lower alkyl is butyl, such as n-butyl, sec-butyl, isobutyl, tert-butyl, propyl, such as n-propyl or isopropyl, ethyl or methyl. For example lower alkyl is methyl, propyl or tert-butyl.

Lower acyl is for example formyl or lower alkylcarbonyl, in particular acetyl.

An aryl group is an aromatic radical which is bound to the molecule via a bond located at an aromatic ring carbon atom of the radical. In an exemplary embodiment, aryl is an aromatic radical having six to fourteen carbon atoms, especially phenyl, naphthyl, tetrahydronaphthyl, fluorenyl or phenanthrenyl, and is unsubstituted or substituted by one or more, for example up to three, especially one or two substituents, especially selected from amino, mono- or disubstituted amino, halogen, lower alkyl, substituted lower alkyl, lower alkenyl, lower alkynyl, phenyl, hydroxy, etherified or esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenylthio, phenyl-lower alkylthio, lower alkylphenylthio, lower alkylsulfinyl, phenylsuffinyl, phenyl-lower alkylsulfinyl, lower alkylphenylsulfinyl, lower alkylsulfonyl, phenylsulfonyl, phenyl-lower alkylsulfonyl, lower alkylphenylsulfonyl, halogen-lower alkylmercapto, halogen-lower alkylsulfonyl, such as especially trifluoromethanesulfonyl, dihydroxybora (—B(OH)2), heterocyclyl, a mono- or bicyclic heteroaryl group and lower alkylene dioxy bound at adjacent C-atoms of the ring, such as methylene dioxy. Aryl is for example phenyl, naphthyl or tetrahydronaphthyl, which in each case is either unsubstituted or independently substituted by one or two substituents selected from the group comprising halogen, especially fluorine, chlorine, or bromine; hydroxy; hydroxy etherified by lower alkyl, e.g. by methyl, by halogen-lower alkyl, e.g. trifluoromethyl, or by phenyl; lower alkylene dioxy bound to two adjacent C-atoms, e.g. methylenedioxy, lower alkyl, e.g. methyl or propyl; halogen-lower alkyl, e.g. trifluoromethyl; hydroxy-lower alkyl, e.g. hydroxymethyl or 2-hydroxy-2-propyl; lower alkoxy-lower alkyl; e.g. methoxymethyl or 2-methoxyethyl; lower alkoxy-carbonyl-lower alkyl, e.g. methoxy-carbonylmethyl; lower alkynyl, such as 1-propynyl; esterified carboxy, especially lower alkoxycarbonyl, e.g. methoxycarbonyl, n-propoxy carbonyl or iso-propoxy carbonyl; N-mono-substituted carbamoyl, in particular carbamoyl monosubstituted by lower alkyl, e.g. methyl, n-propyl or iso-propyl; amino; lower alkylamino, e.g. methylamino; di-lower alkylamino, e.g. dimethylamino or diethylamino; lower alkylene-amino, e.g. pyrrolidino or piperidino; lower oxaalkylene-amino, e.g. morpholino, lower azaalkylene-amino, e.g. piperazino, acylamino, e.g. acetylamino or benzoylamino; lower alkylsulfonyl, e.g. methylsulfonyl; sulfamoyl; or phenylsulfonyl.

A cycloalkyl group is for example cyclopropyl, cyclopentyl, cyclohexyl or cycloheptyl, and may be unsubstituted or substituted by one or more, especially one or two, substitutents selected from the group defined above as substituents for aryl, e.g., by lower alkyl, such as methyl, lower alkoxy, such as methoxy or ethoxy, or hydroxy, and further by oxo or fused to a benzo ring, such as in benzcyclopentyl or benzcyclohexyl.

Substituted alkyl is alkyl as last defined, especially lower alkyl, for example methyl; where one or more, especially up to three, substituents may be present, primarily from the group selected from halogen, especially fluorine, amino, N-lower alkylamino, N,N-di-lower alkylamino, N-lower alkanoylamino, hydroxy, cyano, carboxy, lower alkoxycarbonyl, and phenyl-lower alkoxycarbonyl. Trifluoromethyl is especially useful.

Mono- or disubstituted amino is especially amino substituted by one or two radicals selected independently of one another from lower alkyl, such as methyl; hydroxy-lower alkyl, such as 2-hydroxyethyl; lower alkoxy lower alkyl, such as methoxy ethyl; phenyl-lower alkyl, such as benzyl or 2-phenylethyl; lower alkanoyl, such as acetyl; benzoyl; substituted benzoyl, wherein the phenyl radical is especially substituted by one or more, for example one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and phenyl-lower alkoxycarbonyl, wherein the phenyl radical is unsubstituted or especially substituted by one or more, for example one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and is for example N-lower alkylamino, such as N-methylamino, hydroxy-lower alkylamino, such as 2-hydroxyethylamino or 2-hydroxypropyl, lower alkoxy lower alkyl, such as methoxy ethyl, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, or a substituent selected from the group comprising benzoylamino and phenyl-lower alkoxycarbonylamino, wherein the phenyl radical in each case is unsubstituted or especially substituted by nitro or amino, or also by halogen, amino, N-lower alkylamino, N,N-di-lower alkylamino, hydroxy, cyano, carboxy, lower alkoxycarbonyl, lower alkanoyl, carbamoyl or aminocarbonylamino. Disubstituted amino is also lower alkylene-amino, e.g. pyrrolidino, 2-oxopyrrolidino or piperidino; lower oxaalkylene-amino, e.g. morpholino, or lower azaalkylene-amino, e.g. piperazino or N-substituted piperazino, such as N-methylpiperazino or N-methoxycarbonylpiperazino.

Halogen is especially fluorine, chlorine, bromine, or iodine, especially fluorine, chlorine, or bromine.

Etherified hydroxy is especially $C_8$-$C_{20}$alkyloxy, such as n-decyloxy, lower alkoxy, such as methoxy, ethoxy, isopropyloxy, or tert-butyloxy, phenyl-lower alkoxy, such as benzyloxy, phenyloxy, halogen-lower alkoxy, such as trifluoromethoxy, 2,2,2-trifluoroethoxy or 1,1,2,2-tetrafluoroethoxy, or lower alkoxy which is substituted by mono- or bicyclic hetero-aryl comprising one or two nitrogen atoms, for example lower alkoxy which is substituted by imidazolyl, such as 1H-imidazol-1-yl, pyrrolyl, benzimidazolyl, such as 1-benzimidazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, indolyl or thiazolyl.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxycarbonyloxy.

Esterified carboxy is especially lower alkoxycarbonyl, such as tert-butoxycarbonyl, iso-propoxycarbonyl, methoxycarbonyl or ethoxycarbonyl, phenyl-lower alkoxycarbonyl, or phenyloxycarbonyl.

Alkanoyl is primarily alkylcarbonyl, especially lower alkanoyl, e.g. acetyl.

N-Mono- or N,N-disubstituted carbamoyl is especially substituted by one or two substituents independently selected from lower alkyl, phenyl-lower alkyl and hydroxy-lower alkyl, or lower alkylene, oxa-lower alkylene or aza-lower alkylene optionally substituted at the terminal nitrogen atom.

A mono- or bicyclic heteroaryl group comprising zero, one, two or three ring nitrogen atoms and zero or one oxygen atom and zero or one sulfur atom, which groups in each case are unsubstituted or mono- or polysubstituted, refers to a heterocyclic moiety that is unsaturated in the ring binding the heteroaryl radical to the rest of the molecule in formula I and is for example a ring, where in the binding ring, but optionally also in any annealed ring, at least one carbon atom is replaced by a heteroatom selected from the group consisting of nitrogen, oxygen and sulfur; where the binding ring for example has five to twelve, e.g., five or six ring atoms; and which may be unsubstituted or substituted by one or more, especially one or two, substitutents selected from the group defined above as substitutents for aryl, most for example by lower alkyl, such as methyl, lower alkoxy, such as methoxy or ethoxy, or hydroxy. For example the mono- or bicyclic heteroaryl group is selected from 2H-pyrrolyl, pyrrolyl, imidazolyl, benzimidazolyl, pyrazolyl, indazolyl, purinyl, pyridyl, pyrazinyl, pyrimidinyl, pyridazinyl, 4H-quinolizinyl, isoquinolyl, quinolyl, phthalazinyl, naphthyridinyl, quinoxalyl, quinazolinyl, quinnolinyl, pteridinyl, indolizinyl, 3H-indolyl, indolyl, isoindolyl, oxazolyl, isoxazolyl, thiazolyl, isothiazolyl, triazolyl, tetrazolyl, furazanyl, benzo[d]pyrazolyl, thienyl and furanyl. For example the mono- or bicyclic heteroaryl group is selected from the group consisting of pyrrolyl, imidazolyl, such as 1H-imidazol-1-yl, benzimidazolyl, such as 1-benzimidazolyl, indazolyl, especially 5-indazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, especially 4- or 8-quinolinyl, indolyl, especially 3-indolyl, thiazolyl, benzo[d]pyrazolyl, thienyl, and furanyl. In one exemplary embodiment of the invention the pyridyl radical is substituted by hydroxy in ortho position to the nitrogen atom and hence exists at least partially in the form of the corresponding tautomer which is pyridin-(1H)2-one. In another exemplary embodiment, the pyrimidinyl radical is substituted by hydroxy both in position 2 and 4 and hence exists in several tautomeric forms, e.g. as pyrimidine-(1H, 3H)2,4-dione.

Heterocyclyl is especially a five, six or seven-membered heterocyclic system with one or two heteroatoms selected from the group comprising nitrogen, oxygen, and sulfur, which may be unsaturated or wholly or partly saturated, and is unsubstituted or substituted especially by lower alkyl, such as methyl, phenyl-lower alkyl, such as benzyl, oxo, or heteroaryl, such as 2-piperazinyl; heterocyclyl is especially 2- or 3-pyrrolidinyl, 2-oxo-5-pyrrolidinyl, piperidinyl, N-benzyl-4-piperidinyl, N-lower alkyl-4-piperidinyl, N-lower alkyl-piperazinyl, morpholinyl, e.g. 2- or 3-morpholinyl, 2-oxo-1H-azepin-3-yl, 2-tetrahydrofuranyl, or 2-methyl-1,3-dioxolan-2-yl.

Salts are especially the pharmaceutically acceptable salts of compounds of formula I.

Such salts are formed, for example, as acid addition salts, for example with organic or inorganic acids, from compounds of formula I with a basic nitrogen atom, especially the pharmaceutically acceptable salts. Suitable inorganic acids include, but are not limited to, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of formula I may also form internal salts.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore particularly useful.

In view of the close relationship between the novel compounds in free form and those in the form of their salts, including those salts that may be used as intermediates, for example in the purification or identification of the novel compounds, any reference to the free compounds hereinbefore and hereinafter is to be understood as referring also to the corresponding salts, as appropriate and expedient.

Compounds within the scope of formula I and the process for their manufacture are disclosed in WO 04/005281, published on Jan. 15, 2004, which is hereby incorporated in its entirety into the present application by reference. A particularly useful therapeutic compound in the present invention is 4-Methyl-3-[[4-(3-pyridinyl)-2-pyrimidinyl]amino]-N-[5-(4-methyl-1H-imidazol-1-yl)-3-(trifluoromethyl)phenyl] benzamide (also known as nilotinib) which has the structure:

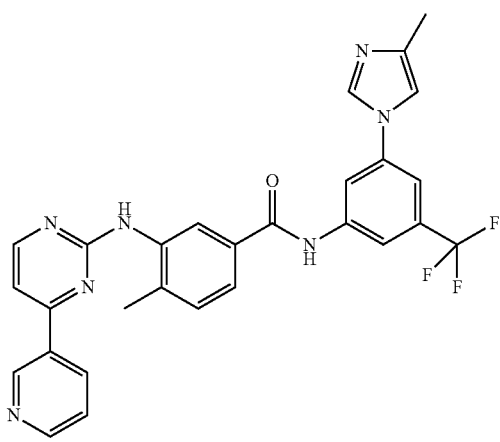 [SMILES: Cc1cn(-c2cc(NC(=O)c3ccc(C)c(Nc4nccc(-c5cccnc5)n4)c3)cc(C(F)(F)F)c2)cn1]

A particularly useful salt of nilotinib is nilotinib hydrochloride monohydrate, or 4-Methyl-N-[3-(4-methyl-1H-imidazol-1-yl)-5-(trifluromethyl)phenyl]-3-[(4-pyridine-3-ylpyrimidin-2-yl)amino]benzamide hydrochloride hydrate. Suitable salts of nilotinib and polymorphs thereof are disclosed in more general in WO2007/015870 and WO2007/015871.

As used herein the term "pharmaceutical composition" means, for example, a mixture containing a specified amount of a therapeutic compound, e.g. a therapeutically effective amount, of a therapeutic compound in a pharmaceutically acceptable carrier to be administered to a mammal, e.g., a human in order to treat kinase dependent diseases.

As used herein the term "pharmaceutically acceptable" refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio.

The concentration of therapeutic compound in the pharmaceutical composition is present in an amount, e.g. in a therapeutically effective amount, which will depend on absorption, inactivation and excretion rates of the drug as well as other factors known to one of ordinary skill in the art. Furthermore, it is to be noted that dosage values will also vary with the severity of the condition to be alleviated. It is to be further understood that for any particular recipient, specific dosage regimens should be adjusted over time according to the individual need and the professional judgment of the person administering or supervising the administration of the pharmaceutical compositions. The therapeutic compound may be administered once, or may be divided into a number of smaller doses to be administered at varying intervals of time. Thus, an appropriate amount, e.g. an appropriate therapeutically effective amount, is known to one of ordinary skill in the art.

For example, the dose of the therapeutic compound will be in the range from about 0.1 to about 100 mg per kilogram body weight of the recipient per day. Alternatively lower doses may be given, for example doses of 0.5 to 100 mg; 0.5 to 50 mg; or 0.5 to 20 mg per kilogram body weight per day. The effective dosage range of the pharmaceutically acceptable salts may be calculated based on the weight of the active moiety to be delivered. If the salt exhibits activity itself, the effective dosage may be estimated as above using the weight of the salt, or by other means known to those skilled in the art.

As used herein the term "immediate-release" refers to the rapid release of the majority of the therapeutic compound, e.g., greater than about 50%, about 55%, about 60%, about 65%, about 70%, about 75%, about 80%, or about 90% within a relatively short time, e.g., within 1 hour, 40 minutes, 30 minutes or 20 minutes after oral ingestion. Particularly useful conditions for immediate-release are release of at least or equal to about 80% of the therapeutic compound within thirty minutes after oral ingestion. The particular immediate-release conditions for a specific therapeutic compound will be recognized or known by one of ordinary skill in the art.

As used herein the term "excipient" refers to a pharmaceutically acceptable ingredient that is commonly used in the pharmaceutical technology for preparing granule and/or solid oral dosage formulations. Examples of categories of excipients include, but are not limited to, binders, disintegrants, lubricants, glidants, stabilizers, fillers and diluents. One of ordinary skill in the art may select one or more of the aforementioned excipients with respect to the particular desired properties of the granule and/or solid oral dosage form by routine experimentation and without any undue burden. The amount of each excipient used may vary within ranges conventional in the art. The following references which are all hereby incorporated by reference disclose techniques and excipients used to formulate oral dosage forms. See *The Handbook of Pharmaceutical Excipients*, 4$^{th}$ edition, Rowe et al., Eds., American Pharmaceuticals Association (2003); and *Remington: the Science and Practice of Pharmacy*, 20$^{th}$ edition, Gennaro, Ed., Lippincott Williams & Wilkins (2000).

As used herein, the term "wet granulation" refers to the general process of using a granulation liquid in the granulation process to subsequently form granules, as discussed in *Remington: The Science and Practice of Pharmacy*, 20$^{th}$ Edition (2000), Chapter 45, which is hereby incorporated by reference.

In an exemplary embodiment of the present invention, wet granulation includes the steps of mixing; wetting and kneading, i.e., wet massing; granulating (i.e. kneading in case of a high shear mixture); drying; and sieving. These steps are discussed in more detail below.

The wet granulation process begins with the formation of a powder blend of the therapeutic compound and at least one pharmaceutically acceptable excipient, especially a surfactant, by mixing with, for example pharmaceutical granulation equipment, the aforementioned ingredients (i.e. bringing into intimate proximity) in a suitable container, so as to form a mixture. Examples of pharmaceutical granulation equipment include, but are not limited to, shear granulators (e.g., Hobart, Collette, Beken) in combination with an oscillating granulator; high speed mixers/granulators (e.g., Diosna, Fielder, Collette-Gral), and fluid-bed granulators (e.g., Aeromatic, Glatt) with a subsequent sieving equipment. Excipients useful for initially mixing with the therapeutic compound include, for example, surfactants, binders, fillers, disintegrants, diluents, and any combinations of the foregoing. Particularly useful in the powder blend mixture are surfactants.

Examples of pharmaceutically acceptable surfactants include, but are not limited to, polyoxyethylene-polyoxypropylene block copolymers (also known as poloxamers), alkyl sulfates (e.g., sodium lauryl sulfate, sodium stearyl sulfate, sodium oleyl sulfate and sodium cetyl sulfate), alkyl aryl sulfonates (e.g., sodium dodecylbenzene sulfonate and dialkyl sodium sulfosuccinates), polyethylene glycols and polysorbates. As used herein the term "poloxamer" refers to at least one polymer having the formula: $HO(C_2H_4)_a(C_3H_6O)_b(C_2H_4O)_aH$ in which "a" and "b" denote the number of polyoxyethlene and polyoxypropylene units respectively. Particularly useful is poloxamer 188 which has an a and b value of 75 and 30 respectively. The surfactant may be present in a concentration of 0 to about 1% by weight of the composition (e.g., by the weight of the capsule fill weight).

Examples of pharmaceutically acceptable disintegrants include, but are not limited to, starches; clays; celluloses;

alginates; gums; cross-linked polymers, e.g., cross-linked polyvinyl pyrrolidone or crospovidone, e.g., POLYPLASDONE XL from International Specialty Products (Wayne, N.J.); cross-linked sodium carboxymethylcellulose or croscarmellose sodium, e.g., AC-DI-SOL from FMC; and cross-linked calcium carboxymethylcellulose; soy polysaccharides; and guar gum. The disintegrant may be present in a concentration from about 0 to about 50% by weight of the composition (e.g., by and bapsule fill weight).

Examples of pharmaceutically acceptable binders include, but are not limited to, starches; celluloses and derivatives thereof, for example, microcrystalline cellulose, e.g., AVICEL PH from FMC (Philadelphia, Pa.), hydroxypropyl cellulose hydroxylethyl cellulose and hydroxylpropylmethyl cellulose, e.g. METHOCEL from Dow Chemical Corp. (Midland, Mich.); sucrose; dextrose; corn syrup; polysaccharides; povidone and gelatin. The binder may be present in a concentration from about 0 to about 50% by weight of the composition (e.g., by the capsule fill weight).

Examples of pharmaceutically acceptable fillers and pharmaceutically acceptable diluents include, but are not limited to, confectioner's sugar, compressible sugar, dextrates, dextrin, dextrose, lactose, mannitol, microcrystalline cellulose, powdered cellulose, sorbitol, and sucrose. The filler may be present in a concentration from about 0 to about 80% by weight of the composition (e.g., by the capsule fill weight).

Sticking problems were observed with the capsules of the present invention during automatic capsule filling. Surprisingly it was found that capsules containing lactose monohydrate in an amount of less than about 40% by weight of the composition do not have such sticking problems. Hence, in one embodiment, the present invention relates to capsules as described herein containing lactose monohydrate in an amount of less than about 40% w/w of the total weight of the capsule; more specifically in an amount of less than about 25%, more preferably an amount of less than about 20%, w/w of the external phase of the capsule.

The next step is wet massing the powder blend by adding a granulation liquid while agitating the powder blend until the powder blend is wetted with the granulation liquid to form a wet mass. For example, 10% to 35% (w/w) granulation liquid is added to the powder blend. Alternatively, 10% to 15% (w/w) granulation liquid may be added to the powder blend. The granulation liquid, for example is pharmaceutically acceptable and volatile. Examples of suitable granulation liquids include, but are not limited to, water (e.g. purified water), organic solvents (e.g., methanol, ethanol, isopropanol, acetone) either alone or in combination. An example of a combination granulation liquid includes water, ethanol and isopropanol together.

Alternatively, the wet granulation process may begin with the therapeutic compound as a powder by itself.

During wet massing, the granulation liquid that is introduced to the powder is a solvent containing or not one or several dissolved excipient, e.g. a binder and/or a surfactant. Irrespective of how wet-massing takes place, after wet-massing, the powder blend is wetted by the granulation liquid. In one exemplary embodiment, purified water is used as the granulation liquid.

Subsequently after processing with the granulation liquid, the wet mass may be optionally sieved forming moist, or damp, granules. The wet mass, for example, may be sieved through a mesh, such as a 5 to up to 10 mm, e.g. 6- or 8-mesh screen. One of ordinary skill in the art may select the appropriate size of the screen in order to form the most appropriate granule size.

In an alternative embodiment, a comminuting mill may be used in lieu of the screen or sieve. Examples of a comminuting mill include, but are not limited to, a Stokes oscillator, a Colton rotary granulator, a Fitzpatrick comminuting mill, a Stokes tornado mill).

In yet another alternative embodiment, a high-speed mixer equipped with, for example a chopper blade, may be used to replace either the screen or the comminuting mill. In this case, the granulating step is called kneading. This, for example, allows the wet massing and granulating to be combined into a single step.

The moist granules, for example, are subsequently dried. For example, the moist granules may be collected on trays and transferred to a drying oven. Alternatively, the moist granules may be placed in a drying cabinet with circulating air current and thermostatic heat control. Yet another option is to dry the moist granules in a fluid-bed drier. In this exemplary embodiment, the moist granules are suspended and agitated in a warm air stream such that the moist granules are maintained in motion. For example, the air temperature may be from about room temperature to about 90° C., e.g. 70° C. The moist granules are dried to a loss on drying ("LOD") value less than or equal to about five percent, e.g., less than two percent, e.g., 0.5 to 2%, by weight of the composition.

Yet another option is a single pot process with granulation and drying in the same equipment (for example, a high shear mixer with a double wall for drying like a Zanchetta Roto P or Turbosphere Moritz).

Drying may take place within or apart from the pharmaceutical granulation equipment.

Subsequent to drying, the granule may be further sieved, i.e., dry screened, alone or in combination with at least one excipient. This typically results in a more uniform particle size of granules, preparing the granules for further processing into a solid oral dosage form.

The granules may be formulated with additional pharmaceutically acceptable excipients to form an intimate mixture that is subsequently formed into an oral form, e.g., solid oral dosage forms, such as tablets, pills, lozenges, caplets, capsules or sachets. As used herein, the term "external phase" refers to the additional excipients that are added to the granules prior to forming the final dosage form. Any additional excipients used may be sieved separately from the granules or concurrently with the sieving of the granules as described in the aforementioned dry sieving step. One of ordinary skill in the art will appreciate the necessary particle size of each component that is necessary for the particular pharmaceutical composition being formulated. For example, suitable particle sizes, include those of less than equal to 1,000 μm, 750 μm, 500 μm or 250 μm. Assembling of the granules with the external phase into an intimate mixture may be accomplished using any conventional pharmaceutical process as known by one of ordinary skill in the art, for example, blending, compressing, co-milling, compacting, or co-micronizing.

The blended mixture may, for example, be subsequently compacted into a tablet (e.g., by using a tablet press) or filled into a capsule or sachet (e.g., by using encapsulating machinery). Any capsules as known in the art may be used to encapsulate the blended mixture. An example of such a capsule is hard gelatin capsules, for example CONI-SNAP manufactured by Capsugel of Morris Plains, N.J. Suitable sizes for such capsules include, but are not limited to sizes Nos. 00 through 5. Pharmaceutical compositions in the form of capsules may contain, for example, from 5 mg to 500 mg of therapeutic compound per capsule; e.g., 25 mg, 50 mg, 100 mg or 200 mg therapeutic compound per capsule.

A commonly used pharmaceutically acceptable excipient to add in the external phase is a glidant. Such an excipient facilitates the flow of the blended mixture in the processing equipment.

Examples of pharmaceutically acceptable glidants include, but are not limited to, colloidal silica, magnesium trisilicate, starches, talc, tribasic calcium phosphate, aluminium stearate, magnesium carbonate, magnesium oxide and powdered cellulose. The glidant may be present in a concentration from about 0 to 10%, e.g. from 0 to 10%, alternatively about 1%, e.g. 1%, by weight of the total weight of the pharmaceutical composition.

Another commonly used pharmaceutically acceptable excipient to add to the external phase is a lubricant. Such an excipient helps to avoid any sticking in the processing equipment. Although a lubricant enhances processability, it may impact the release of the therapeutic compound from the dosage form. Often, a lubricant is hydrophobic and consequently retards or slows down the release of a therapeutic compound in an immediate release dosage form. Surprisingly it has been found that the inclusion of a surfactant during the wet granulation process results in granules that are better processable, and allows for a reduction of lubricant. This reduction of lubricant concentration results in a pharmaceutical composition with a better dissolution profile than if no surfactant is used. Without being bound to any particular theory, the use of a lubricant may prevent access of water to the other excipients due to its hydrophobicity, and consequently slow down solubilization. For example, in exemplary embodiments of the present invention, the concentration of the lubricant is less than 1% by weight of the pharmaceutical composition, e.g., 0.5%.

Examples of lubricants, e.g. pharmaceutically acceptable lubricants include, but are not limited to, talc, magnesium stearat, aluminuim stearate, calcium stearate, magnesium carbonate, polyethylene glycol, glyceryl behenate, stearic acid, hydrogenated castoril, glyceryl monostearate and sodium stearyl fumarate. The lubricant may be present in a concentration form about 0 to 10%, e.g. 0 to 10%, alternatively about 2%, e.g. 2%, by weight of the total weight of the pharmaceutical composition.

The following examples are illustrative, but do not serve to limit the scope of the invention described herein. The examples are meant only to suggest a method of practicing the present invention.

Quantities of ingredients, represented by percentage by weight of the pharmaceutical composition, used in each example are set forth in the respective tables located after the respective descriptions. For a capsule, when calculating the weight of the pharmaceutical composition (i.e. the capsule fill weight), the weight of the capsule shell itself is excluded from the calculation.

Example 1

The therapeutic compound in this example is nilotinib hydrochloride monohydrate. This therapeutic compound has low solubility in aqueous media. Furthermore this therapeutic compound has a slight hygroscopic tendency.

Table 1 shows the formulation of Example 1

| Ingredients | Amount per capsule (mg) | Percentage (w%/w%) |
|---|---|---|
| Granule | | |
| Nilotinib hydrochloride monohydrate | 220.60 | 55.2% |
| Poloxamer 188 | 3.18 | 0.8 |
| Lactose monohydrate | 78.47 | 19.6% |
| Polyvinyl pyrrolidone | 15.91 | 4% |

-continued

| Ingredients | Amount per capsule (mg) | Percentage (w%/w%) |
|---|---|---|
| External Phase | | |
| Lactose monohydrate | 77.64 | 19.4% |
| Colloidal silicon dioxide | 2.10 | 0.5% |
| magnesium stearate | 2.10 | 0.5% |
| Total | 400.0 | |

The nilotinib hydrochloride monohydrate, lactose monohydrate and polyvinyl pyrrolidone are mixed together using a high shear mixer to form a powder blend. The poloxamer 188 is solubilized with purified water and then added to the powder blend in order to wet the powder blend. Then, the mixture is kneaded and dried in a fluid bed dryer to form granules. Lactose monohydrate and colloidal silicon dioxide (as part of the external phase) are screened along with the granules using an oscillating granulator with a 0.8 mm screen. A bin blender is used to provide additional blending. Magnesium stearate is separately sieved on a 0.9 mm screen and added to the mixture for final blending. The blended mixture is filled into capsules.

Because of the slight hygroscopic tendency of the nilotinib hydrochloride monohydrate, it may be expected that the filled hard gelatin capsule shells would deform over aging. Surprisingly, the physical stability of the filled hard gelatin capsules did not substantially deform during visual inspection during accelerated aging (i.e., subjecting the capsules to higher temperatures and conditions of relative humidity (40° C./75% RH)). Preferably, in order to achieve this stability, the water content of the capsules should so low that upon drying the capsules for 10 min at 80° C. the loss of weight should be lower than 3.0%.

Sticking problems were observed with the capsules of the present invention during automatic capsule filling. Surprisingly it was found that capsules containing lactose monohydrate in an amount of less than about 40% w/w of the total weight of the capsule do not have such sticking problems.

Example 2

Dissolution Profile

Dissolution testing is performed using the basket method according to Ph. Eur. 2.9.3 'Dissolution test for solid dosage forms' and USP <711> 'Dissolution' at 100 rpm in 1000 ml 0.1 N HCL as dissolution material. The determination of the amount of drug substance dissolved (%) is performed with a UV detection method. The method has been validated for selectivity, accuracy, precision and linearity.

TABLE 2

Dissolution Results of the Capsule of Example 1

| Time Point (min) | Mean of Nilotinib hydrochloride monohydrate dissolved in % |
|---|---|
| 5 | 29.8 |
| 15 | 97.2 |
| 30 | 98.5 |
| 60 | 99.1 |

It is understood that while the present invention has been described in conjunction with the detailed description thereof that the foregoing description is intended to illustrate and not limit the scope of the invention, which is defined by the scope of the following claims. Other aspects, advantages and modifications are within the scope of the claims.

What is claimed:

1. A pharmaceutical composition, in the form of a capsule comprising:
a granule comprising a therapeutic compound in an intimate mixture with at least one pharmaceutically acceptable excipient, wherein said therapeutic compound is a monohydrochloride salt of 4-Methyl-3-[[4-(3-pyridinyl)-2-pyrimidinyl]amino]-N-[5-(4-methyl-1H-imidazol-1-yl)-3-(trifluoromethyl)phenyl]benzamide of formula:

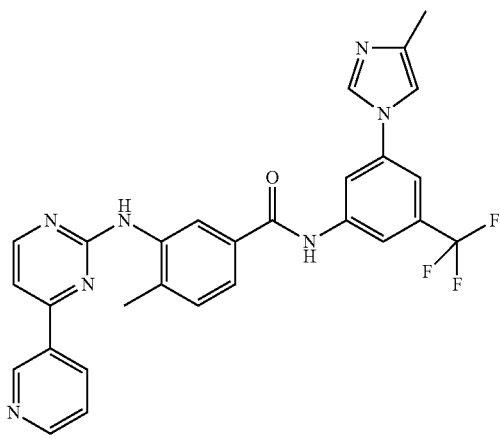 [SMILES: Cc1cn(-c2cc(NC(=O)c3ccc(C)c(Nc4nccc(-c5cccnc5)n4)c3)cc(C(F)(F)F)c2)cn1]

as a monohydrate, wherein said granule further comprises a surfactant and a lubricant, said surfactant is in a concentration from 0 to 1% by weight of said pharmaceutical composition and the concentration of said lubricant does not exceed 1% by weight of the pharmaceutical composition.

2. The pharmaceutical composition of claim 1, wherein said lubricant is magnesium stearate.

3. The pharmaceutical composition of claim 2, wherein said surfactant is a poloxamer.

4. The pharmaceutical composition of claim 3, wherein said poloxamer is poloxamer 188.

5. The pharmaceutical composition of claim 1, wherein said said therapeutic compound and excipients are combined to form granules, which are further dried to form a powder blend of granules.

6. A pharmaceutical composition, in the form of a capsule comprising: 55.2% by weight of monohydrochloride salt of 4-Methyl-3-[[4-(3-pyridinyl)-2-pyrimidinyl]amino]-N-[5-(4-methyl-1H-imidazol-1-yl)-3-(trifluoromethyl)phenyl] benzamide of formula:

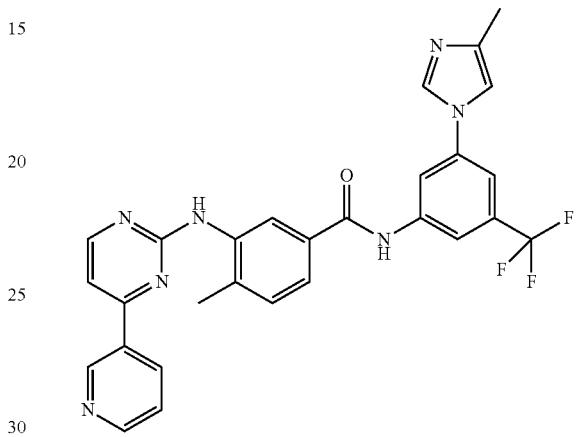

as a monohydrate; 0.8% by weight of a surfactant; 19.6% by weight of a diluent; 4% by weight of a disintegrant; and an external phase further comprising: 19.4% by weight of a diluent; 0.5% by weight of a glidant; and 0.5% by weight of a lubricant and water, wherein water is used as a granulation liquid.

* * * * *